Aug. 16, 1949. E. PRUSHEK Plant Pat. 865
CHRYSANTHEMUM PLANT
Filed April 16, 1948
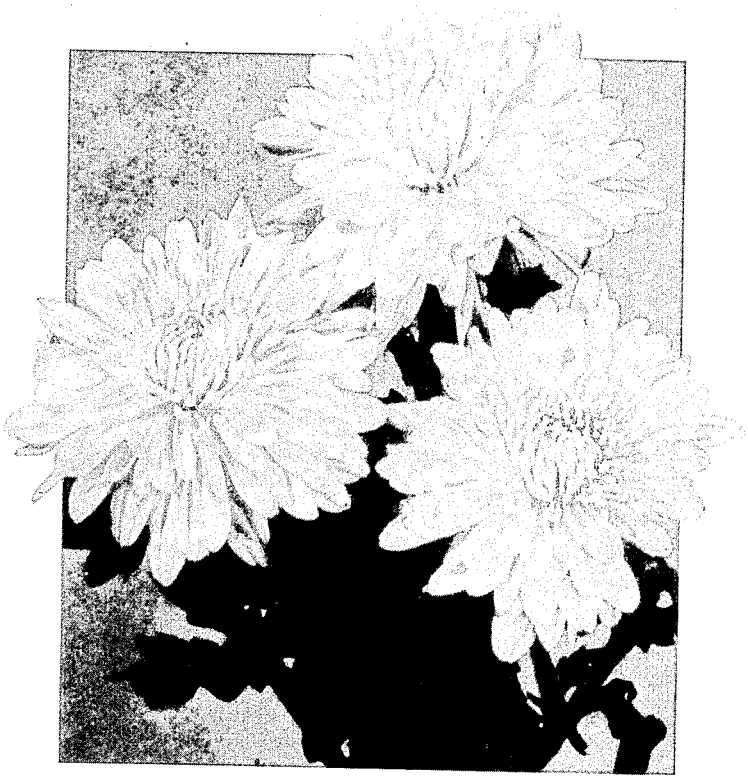
Inventor:
Emil Prushek
By Robert Robb
Attorney Patented Aug. 16, 1949

Plant Pat. 865

UNITED STATES PATENT OFFICE

865

CHRYSANTHEMUM PLANT

Emil Prushek, Niles, Mich., assignor to The R. M. Kellogg Company, Three Rivers, Mich., a corporation of Michigan Application April 16, 1948, Serial No. 21,460

1 Claim. (Cl. 47—60)

The present invention relates to a new and distinct variety of chrysanthemum plant resulting from seed of the variety Princess of Plant Patent No. 711 pollenized with pollen of the same variety.

The object of my invention has been to produce a new variety of chrysanthemum similar to the variety Princess in reference to the dwarf, compact, and floriferous characteristics of the bush or plant form, but having blossoms whose coloring differs from the coloring of the blossoms of the variety Princess. More especially, it has been an object of my invention to produce a new variety of chrysanthemum of the type mentioned having blossoms whose coloring is a distinct "light pink" much in demand by gardeners.

For the accomplishment of the especial purposes above mentioned I have conducted a careful program of inbreeding and selection as an incident to and part of a broader program of selection and cross-breeding which I have been conducting for some time with a view to producing new varieties of chrysanthemums of the type mentioned in a full range of colors. Other examples of new varieties of chrysanthemums of this type which have been produced pursuant to the aforesaid program are the variety Nugget of Plant Patent Application Serial No. 712,882, filed November 29, 1946, now Patent Number 802, issued July 6, 1948, and the variety Honey Chile of Plant Patent application Serial No. 788,743, filed November 28, 1947.

The results of the specific inbreeding program above mentioned have been to produce my present new and distinct variety of chrysanthemum characterized by its dwarf, compact, and floriferous habits of growth, and the lighter purple color of its blooms.

The blooms of my new variety are lilac purple in color. As compared with the blooms of the variety Honey Chile, which are magnolia purple in color, the lilac purple color of the blooms of my new variety is about two tints lighter on the color scale, and lightened by Dresden yellow. The variety Honey Chile and my present new variety of chrysanthemum are, respectively, distinct "dark pink" and "light pink" editions of this type of plant, these "dark pink" and "light pink" colors being much in demand by gardeners.

While my new variety of chrysanthemum is substantially identical with its parent Princess in reference to its dwarf and compact plant form, and its floriferous habit of growth, my new variety differs from its parent in respect to the distinctively different coloring of the blooms and the slightly larger average size of the plant of my new variety. My new variety is perhaps most similar to the variety Honey Chile, my new variety having in general similar dwarf and compact habits of growth, the plants of my new variety having a somewhat larger average size, and the blooms of my new variety having a lighter shade of purple as above mentioned.

My new variety is distinctive when compared with the somewhat similar standard variety Major Cushion, my new variety being characterized by the fact that its plants are more compact, more floriferous, and about one-half the volume as compared with the plants of the Major Cushion variety. Both the Major Cushion and my new variety have blooms which are generally lilac purple in color, but the color of blooms of my new variety is of a lighter tint, with still lighter petal tips and centers lightened by Dresden yellow, making its general color effect a lighter, brighter color (light pink) as compared with the duller, darker (dark pink) shade of Major Cushion.

In its size class my new variety is a strong grower and makes an unusual number of well-rooted sprouts for winter survival and propagation.

For purposes of comparison of my new variety with other varieties, in reference to plant size, I might say that the plants of Major Cushion have average dimensions of 14" in height and 20" in diameter. The Honey Chile variety has average dimensions of the plant of 9" in height and 15" in diameter. The plants of my new variety have average dimensions of 10" in height and 17" in diameter. Thus, my new variety is about one-half of the size or mass of the similar Major Cushion, while plants of the Honey Chile variety are about one-fourth of the size or mass of the similar Major Cushion.

My new variety has been found to retain its distinctive characteristics through successive asexual reproductions.

The accompanying drawing, forming a part hereof, shows a spray of typical blossoms of my new variety.

The following is a detail description of my new variety, all color references being to the horticultural color chart of the British Colour Council:

Classification: Botanic—*Chrysanthemum hortorum.*

*Flower*

Blooming habit: Blooms early; profusely. Recurrent; continuous in the fall.

Bud:

*Size.*—Medium.

*Form.*—Short with flat top. Not affected by wet weather. Not affected by hot weather.

*Color.*—When sepals first divide—Lilac Purple 031/1. When petals begin to unfurl—Lilac Purple 031/2. When half blown—inside of petals: Lilac Purple 031/2; reverse of petals: Lilac Purple 031/3.

*Sepals.*—Smooth edge.

*Calyx.*—Apple shaped.

*Size.*—Broad; small.

*Aspect.*—Hairy.

*Peduncle.*—Short.

*Aspect.*—Rough.

*Color.*—Medium green.

*Strength.*—Stiff, slender.

*Opening.*—Bud opens well; not affected by adverse conditions.

Bloom:

*Size.*—Medium.

*Average size.*—When fully expanded, 2¼".

*Borne.*—Singly.

*Stems.*—Short; normal.

*Form.*—When first open—flat; pompom. *Permanence*—retains its form to the end.

*Petalage.*—Very double. Number of petals under normal conditions, about 200.

*Color.*—Center of flower—Lilac Purple (031/2) lightened by Dresden Yellow (64/2). Outer petals—Lilac Purple (031/3). Base of petals (singlet)—Dresden Yellow (64/2). Inside of petals—Lilac Purple (031/2) tipped by Lilac Purple (031/3). Reverse of petals—Lilac Purple (031/3). General tonality from a distance—Lilac Purple.

*Discoloration.*—First week—none. Second week—slight fading to pleasing Lilac Purple (031/3). Third week—faded.

Petals:

*Texture.*—Thin; soft. Slight fading from wet weather. Not affected by hot weather.

*Appearance.*—Velvety on inside or outside.

*Form.*—Oval; notched.

*Arrangement.*—Imbricated.

*Fragrance.*—Characteristic chrysanthemum.

Genital organs:

*Stamens, anthers.*—Small; few. Color—yellow.

*Stamens, filaments.*—Short. Color—lemon yellow.

*Pollen.*—Gold yellow.

*Stigmas.*—Yellow.

*Plant*

Form: Bush.

Growth: Dwarf; very compact.

Foliage:

*Size.*—Medium.

*Quantity.*—Normal.

*Color.*—New foliage—upper side: normal green; under side: light green.

*Color.*—Old foliage—upper side: normal green; under side: light green.

*Shape.*—Oval.

*Texture.*—Smooth upper side. Under side—rough. Ribs and veins—ordinary.

*Edge.*—Serrated.

*Serration.*—Double; small.

*Leaf stem.*—Green in color. Under side—rough.

Wood:

*New wood.*—Color—light green.

*Old wood.*—Color—green.

I claim:

A new and distinct variety of chrysanthemum plant substantially as herein disclosed, characterized as to novelty by its dwarf, compact, and floriferous habit of growth, and the lighter purple color of its flowers as compared with the Honey Chile variety.

EMIL PRUSHEK.

No references cited.